(12) United States Patent
Tidwell et al.

(10) Patent No.: US 11,897,796 B2
(45) Date of Patent: Feb. 13, 2024

(54) COMPOSITIONS OF HETEROCYCLIC COMPOUNDS AND USES AS SULFIDOGENESIS INHIBITORS

(71) Applicant: ChampionX USA Inc., Sugar Land, TX (US)

(72) Inventors: Timothy James Tidwell, Angleton, TX (US); Alicia Dinges, Houston, TX (US); Ashish Dhawan, Aurora, IL (US)

(73) Assignee: ChampionX USA Inc., Sugarland, TX (US)

( * ) Notice: Subject to any disclaimer, the term of this patent is extended or adjusted under 35 U.S.C. 154(b) by 191 days.

(21) Appl. No.: 17/157,770

(22) Filed: Jan. 25, 2021

(65) Prior Publication Data

US 2021/0238068 A1    Aug. 5, 2021

Related U.S. Application Data

(60) Provisional application No. 62/964,968, filed on Jan. 23, 2020.

(51) Int. Cl.
| | |
|---|---|
| *C02F 1/68* | (2023.01) |
| *C07D 413/06* | (2006.01) |
| *C02F 103/36* | (2006.01) |
| *C09K 8/575* | (2006.01) |

(52) U.S. Cl.
CPC ............ *C02F 1/68* (2013.01); *C07D 413/06* (2013.01); *C09K 8/575* (2013.01); *C02F 2103/365* (2013.01); *C02F 2307/14* (2013.01)

(58) Field of Classification Search
None
See application file for complete search history.

(56) References Cited

U.S. PATENT DOCUMENTS

| | | | |
|---|---|---|---|
| 4,978,512 A | 12/1990 | Dillon | |
| 6,117,364 A * | 9/2000 | Vorderbruggen | ...... C09K 15/06 |
| | | | 507/263 |
| 6,339,153 B1 | 1/2002 | Rivers et al. | |
| 8,864,853 B2 | 10/2014 | Beilfuss et al. | |
| 10,098,346 B2 | 10/2018 | Geissler et al. | |
| 10,119,079 B2 | 11/2018 | Fuji et al. | |
| 10,294,428 B2 | 5/2019 | Suzuki et al. | |
| 10,301,553 B2 | 5/2019 | Geissler et al. | |
| 2013/0131387 A1* | 5/2013 | Kaplan | ............ C02F 1/683 |
| | | | 203/91 |
| 2015/0041411 A1 | 2/2015 | Gradtke et al. | |
| 2015/0104349 A1* | 4/2015 | Leinweber | ........... C07D 239/04 |
| | | | 544/335 |
| 2016/0175769 A1 | 6/2016 | Kamoun et al. | |
| 2018/0030041 A1 | 2/2018 | Beilfuss et al. | |
| 2018/0127638 A1* | 5/2018 | Thompson-Colón | ....................... |
| | | | C07D 231/12 |
| 2018/0346357 A1 | 12/2018 | Gradtke et al. | |
| 2018/0371334 A1 | 12/2018 | Beilfuss et al. | |
| 2019/0194551 A1* | 6/2019 | de Oliveira Filho | .. C10G 29/22 |
| 2019/0233739 A1 | 8/2019 | Beilfuss et al. | |
| 2019/0329175 A1 | 10/2019 | Shimizu et al. | |
| 2020/0109112 A1* | 4/2020 | Moloney | .............. C07D 213/32 |

FOREIGN PATENT DOCUMENTS

| | | |
|---|---|---|
| CN | 107866147 A | 4/2018 |
| WO | 1990007467 A1 | 7/1990 |
| WO | WO-9802501 A1 * | 1/1998 ............. C10G 29/20 |
| WO | 2018/001629 A1 | 1/2018 |

OTHER PUBLICATIONS

Saji, V. S. (2019). Research advancements in sulfide scavengers for oil and gas sectors, Reviews in Chemical Engineering, 20190049. doi: https://doi.org/10.1515/revce-2019-0049, Abstract only.
Markfoged, Rikke, et al. "Considerations for Evaluating Biocidal Efficacy on Biofilm Formation of Oilfield Relevant Microorganisms." Oilfield Microbiology. CRC Press, 2019—Abstract only.
International Search Report and Written Opinion dated May 12, 2021 relating to PCT Application No. PCT/US2021/014929, 11 pages.

* cited by examiner

*Primary Examiner* — John J Figueroa
(74) *Attorney, Agent, or Firm* — Stinson LLP

(57) ABSTRACT

The present disclosure generally relates to compositions and uses of sulfidogenesis inhibitor compounds of Formulae 1 and 2 for preventing sulfidogenesis, i.e., the reduction reaction of a sulfur-containing compound by sulfur-utilizing prokaryotes that produce sulfide species such as hydrogen sulfide, during enhanced oil recovery processes. A method for inhibiting or decreasing microbial sulfide production by sulfur-utilizing prokaryotes includes addition of an effective amount of sulfidogenesis inhibitor compounds of Formulae 1 and 2 to the fluid that is injected into a sulfidogenic reservoir system during enhanced oil recovery. For example, the compounds can be used as sulfidogenesis inhibitors in a water injection system for use in a hydrocarbon extraction system or a hydrocarbon production system. Thus, these compositions can be effectively used as inhibitors of biogenic hydrogen sulfide generation in oilfield fluids.

18 Claims, No Drawings

COMPOSITIONS OF HETEROCYCLIC COMPOUNDS AND USES AS SULFIDOGENESIS INHIBITORS

CROSS REFERENCE TO RELATED APPLICATIONS

This application claims priority to U.S. Provisional Patent Application Ser. No. 62/964,968 filed on Jan. 23, 2020, the disclosure of which is incorporated herein by reference in its entirety.

FIELD

The present disclosure generally relates to compositions and uses of sulfidogenesis inhibitor compounds of Formulae 1 and 2 for preventing sulfidogenesis, i.e., the reduction reaction of a sulfur-containing compound by sulfur-utilizing prokaryotes that produce sulfide species such as hydrogen sulfide, during enhanced oil recovery processes. A method for inhibiting or decreasing microbial sulfide production by sulfur-utilizing prokaryotes includes addition of an effective amount of sulfidogenesis inhibitor compounds of Formulae 1 and 2 to the fluid that is injected into a sulfidogenic reservoir system during enhanced oil recovery. For example, the compounds can be used as sulfidogenesis inhibitors in a water injection system for use in a hydrocarbon extraction system or a hydrocarbon production system. Thus, these compositions can be effectively used as inhibitors of biogenic hydrogen sulfide generation in oilfield fluids.

BACKGROUND

The introduction of sulfate- and sulfur-containing waters into oil fields for enhanced oil recovery often leads to formation of undesirable sulfur-containing compounds, particularly hydrogen sulfide, by sulfur-utilizing prokaryotes. These sulfur-containing compounds lead to safety, environmental, corrosion and plugging problems, and even premature abandonment of the oil and gas field.

Particularly, hydrogen sulfide generation begins by introducing sulfate- or other sulfur-containing aqueous solutions such as seawater into an anaerobic environment for indigenous microorganisms and microorganisms contained in the introduced aqueous solutions that are capable of producing hydrogen sulfide.

Hydrogen sulfide is a toxic, corrosive, flammable gas that causes problems in both the upstream and downstream oil and gas industry. Exposure to this gas, even at low concentrations, can cause serious injury or death. Hydrogen sulfide ($H_2S$) in natural gas and crude oil reserves is often accompanied by small amounts of mercaptans (RSH), sulfides ($R_2S$), polysulfides, and carbonyl sulfide (COS). Considerable expense and effort are expended annually to reduce the $H_2S$ content of gas and oil streams to make them suitable for commercial use.

Hydrogen sulfide has an offensive odor, and natural gas and crude oil streams containing substantial amounts of $H_2S$ are considered "sour." In addition to natural gas and petroleum, there are also aqueous fluids that must be treated to reduce or remove $H_2S$, such as wastewater streams. Treatments to reduce or remove $H_2S$ from hydrocarbon or aqueous streams are referred to as "sweetening" treatments because the odor of the processed products is improved by the absence of hydrogen sulfide.

In some cases, nitrate introduction has been used to prevent sulfide formation in waters because specific nitrate-reducing bacteria (NRB) are activated and use volatile fatty acids (VFAs) and the carbon dioxide from dissolved limestone in the formation to produce nitrogen and/or ammonia. Thus, the NRBs could compete with the sulfur-utilizing prokaryotes and more rapidly use the VFAs, resulting in lowered production of sulfide and sulfur-containing compounds by the sulfur-utilizing prokaryotes.

However, this nitrate treatment can cause problems if the treatment is suspended or stopped because the hydrogen sulfide production would resume at the previous concentrations or the hydrogen sulfide production could even increase due to the enhanced biomass present. Additionally, some instances of nitrate application to reduce hydrogen sulfide have increased corrosion due to the incomplete reduction of the applied nitrate. The increased amount of NRBs can also lead to injectivity issues, where the microbial population blocks the injection path of the water into the reservoir.

Thus, a need exists for an effective and efficient method to prevent the biogenic generation of hydrogen sulfide by the microbes responsible for the production of hydrogen sulfide in a hydrocarbon-containing system comprising a hydrocarbon extraction system or a hydrocarbon production system.

SUMMARY

Methods of sulfidogenesis inhibition in a hydrocarbon-containing system comprising a water injection system, a hydrocarbon extraction system, or a hydrocarbon production system are disclosed herein. The methods comprise administering an effective amount of a sulfidogenesis inhibitor compound of Formula 1 into the water injection system, hydrocarbon extraction system or the hydrocarbon production system, the sulfidogenesis inhibitor compound of Formula 1 having a structure corresponding to:

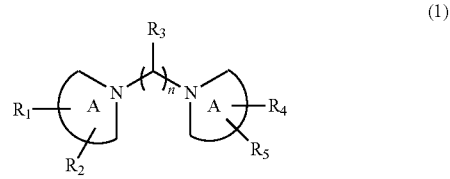

(1)

wherein A is a nitrogen-containing heterocycle of 1,3-oxazetidine, 1,3-diazetidine, 1,3-thiazetidine, oxazolidine, imidazolidine, thiazolidine, 1,3-oxazinane, hexahydropyrimidine, 1,3-thiazinane, 1,3-oxazepane, 1,3-diazepane, 1,3-thiazepane, 1,3-oxazocane, 1,3-diazocane, 1,3-thiazocane; $R_1$, $R_2$, $R_4$, and $R_5$ are independently hydrogen, substituted or unsubstituted alkyl, substituted or unsubstituted aryl, substituted or unsubstituted alkoxy, or substituted or unsubstituted alkaryl; $R_3$ is hydrogen, substituted or unsubstituted alkyl, substituted or unsubstituted aryl, or substituted or unsubstituted alkaryl; and n is an integer from 1 to 10.

For the methods described herein, the sulfidogenesis inhibitor compound of Formula 1 inhibits the production of hydrogen sulfide by a sulfur-utilizing prokaryote.

Further, the sulfur-utilizing prokaryote produces sulfide through reduction of sulfate, thiosulfate, sulfur, bisulfite, an organosulfur compound, or a combination thereof.

For the methods described herein, the sulfidogenesis inhibitor compound of Formula 1 is administered by injecting an injection fluid into the water injection system, the hydrocarbon extraction system or the hydrocarbon production system.

The hydrocarbon extraction system or the hydrocarbon production system treated in the methods disclosed herein is a subterranean hydrocarbon-containing formation, a water injection system, a well, a pipeline, a fluid separation vessel, a floating production storage vessel, an offloading vessel, a refinery, or a storage system. Preferably, the hydrocarbon extraction system or the hydrocarbon production system is a subterranean hydrocarbon-containing formation.

The injection fluid used in the methods comprises seawater, produced water, fresh water, brackish water, drilling fluid, completion fluid, or a combination thereof.

For the sulfidogenesis inhibitor compound of Formula 1 used in the methods and compositions described herein A is oxazolidine, imidazolidine, or thiazolidine.

The sulfidogenesis inhibitor compound of Formula 1 preferably has n be 1.

Methods and compositions containing the sulfidogenesis inhibitor compound of Formula 1 preferably have $R_3$ be hydrogen, methyl, or benzyl.

The sulfidogenesis inhibitor compound of Formula 1 preferably have $R_2$ and $R_4$ are hydrogen and $R_1$ and $R_5$ independently be hydrogen, substituted or unsubstituted $C_1$ to $C_6$ alkyl, substituted or unsubstituted phenyl, or substituted or unsubstituted benzyl. More preferably, $R_2$ and $R_4$ are hydrogen and $R_1$ and $R_5$ are independently hydrogen, unsubstituted $C_1$ to $C_6$ alkyl, unsubstituted phenyl, or unsubstituted benzyl, and most preferably, $R_2$ and $R_4$ are hydrogen and $R_1$ and $R_5$ are independently hydrogen, methyl, ethyl, propyl, butyl, phenyl, or benzyl.

The methods and compositions containing sulfidogenesis inhibitor compounds of Formula 1 preferably contain the sulfidogenesis inhibitor compounds of Formula 2, wherein the compound of Formula 1 has a structure corresponding to Formula 2

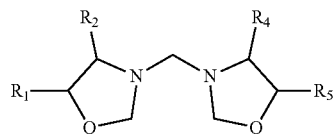

(2)

wherein $R_1$, $R_2$, $R_4$, and $R_5$ are independently hydrogen, substituted or unsubstituted alkyl, substituted or unsubstituted aryl, or substituted or unsubstituted alkaryl.

The methods and compositions used herein have sulfidogenesis inhibitor compounds of Formula 2 that have $R_2$ and $R_4$ are hydrogen and $R_1$ and $R_5$ independently be hydrogen, substituted or unsubstituted $C_1$ to $C_6$ alkyl, or substituted or unsubstituted phenyl. Preferably, $R_2$ and $R_4$ are hydrogen and $R_1$ and $R_5$ are independently hydrogen, unsubstituted $C_1$ to $C_6$ alkyl, or unsubstituted phenyl; more preferably $R_2$ and $R_4$ are hydrogen and $R_1$ and $R_5$ are independently hydrogen, methyl, ethyl, propyl, butyl, phenyl, or benzyl.

For the methods described herein, the effective amount of the sulfidogenesis inhibitor compound of Formula 1 or Formula 2 is from about 1 to about 500 ppm, from about 1 to about 200 ppm, or from about 1 to about 100 ppm based on the total amount of injection fluid injected into the formation or production system.

The sulfidogenesis inhibitor compound of Formula 1 or Formula 2 is injected into the water injection system, the hydrocarbon extraction system, or the hydrocarbon production system continuously with the injection fluid.

Alternatively, the sulfidogenesis inhibitor compound of Formula 1 or Formula 2 is injected into the water injection system, the hydrocarbon extraction system, or the hydrocarbon production system intermittently with the injection fluid. The injection of the compound of Formula 1 or Formula 2 is intermittently injected every one to three hours, every one to three days, or every one to three weeks.

The methods described herein further comprise administering an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof.

Compositions for inhibiting sulfidogenesis of a sulfur-utilizing prokaryote in a hydrocarbon-containing system comprising a water injection system, a hydrocarbon extraction system, or a hydrocarbon production system are also disclosed. The composition comprises an effective amount of a sulfidogenesis inhibitor compound of Formula 1; and an effective amount of a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof; the compound of Formula 1 having a structure corresponding to:

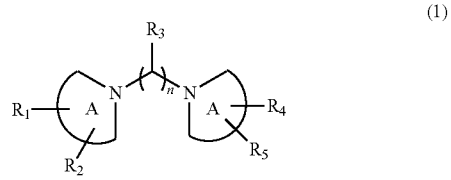

(1)

wherein A is a nitrogen-containing heterocycle of 1,3-oxazetidine, 1,3-diazetidine, 1,3-thiazetidine, oxazolidine, imidazolidine, thiazolidine, 1,3-oxazinane, hexahydropyrimidine, 1,3-thiazinane, 1,3-oxazepane, 1,3-diazepane, 1,3-thiazepane, 1,3-oxazocane, 1,3-diazocane, 1,3-thiazocane; $R_1$, $R_2$, $R_4$, and $R_5$ are independently hydrogen, substituted or unsubstituted alkyl, substituted or unsubstituted aryl, substituted or unsubstituted alkoxy, or substituted or unsubstituted alkaryl; $R_3$ is hydrogen, substituted or unsubstituted alkyl, substituted or unsubstituted aryl, or substituted or unsubstituted alkaryl; and n is an integer from 1 to 10.

The compositions for inhibiting sulfidogenesis of a sulfur-utilizing prokaryote in a hydrocarbon-containing system comprising a water injection system, a hydrocarbon extraction system, or a hydrocarbon production system comprise the sulfidogenesis inhibitor compound of Formula 1 and a biocide.

Other objects and features will be in part apparent and in part pointed out hereinafter.

DESCRIPTION OF THE PREFERRED EMBODIMENTS

The present disclosure is directed to methods for preventing or reducing sulfidogenesis, i.e., the reduction reaction of a sulfur-containing compound by sulfur-utilizing prokaryotes that produce sulfide species such as hydrogen sulfide, during enhanced oil recovery processes. The methods comprise administering an effective amount of a sulfidogenesis inhibitor compound of Formula 1 or 2 into the water injection system, the hydrocarbon extraction system, or the hydrocarbon production system. Oilfield produced fluids or seawater can be treated with the sulfidogenesis inhibitor compounds and compositions described herein that can significantly decrease the amount of biogenic hydrogen sulfide and other reduced sulfur species in the fluids. In particular, the microorganisms can be involved in the reduction reaction of sulfur-containing compounds that produce hydrogen sulfide. The treatment with the compounds and compositions described herein can also significantly decrease the amount of hydrogen sulfide produced by sulfur utilizing prokaryotes. Thus, these compounds and compositions can be effectively used as sulfidogenesis inhibitors in oilfield fluids.

Methods for inhibiting sulfidogenesis in a hydrocarbon-containing system comprising a hydrocarbon extraction system or a hydrocarbon production system are disclosed. The method comprises administering an effective amount of a sulfidogenesis inhibitor compound of Formula 1 into the hydrocarbon extraction system or the hydrocarbon production system, the sulfidogenesis inhibitor compound of Formula 1 having a structure corresponding to:

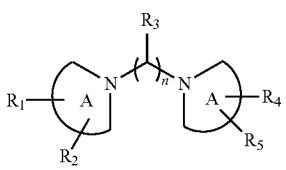

(1)

wherein A is a nitrogen-containing heterocycle of 1,3-oxazetidine, 1,3-diazetidine, 1,3-thiazetidine, oxazolidine, imidazolidine, thiazolidine, 1,3-oxazinane, hexahydropyrimidine, 1,3-thiazinane, 1,3-oxazepane, 1,3-diazepane, 1,3-thiazepane, 1,3-oxazocane, 1,3-diazocane, 1,3-thiazocane; $R_1$, $R_2$, $R_4$, and $R_5$ are independently hydrogen, substituted or unsubstituted alkyl, substituted or unsubstituted aryl, substituted or unsubstituted alkoxy, or substituted or unsubstituted alkaryl; $R_3$ is hydrogen, substituted or unsubstituted alkyl, substituted or unsubstituted aryl, or substituted or unsubstituted alkaryl; and n is an integer from 1 to 10.

For example, the nitrogen-containing heterocycle can have one of the following structures:

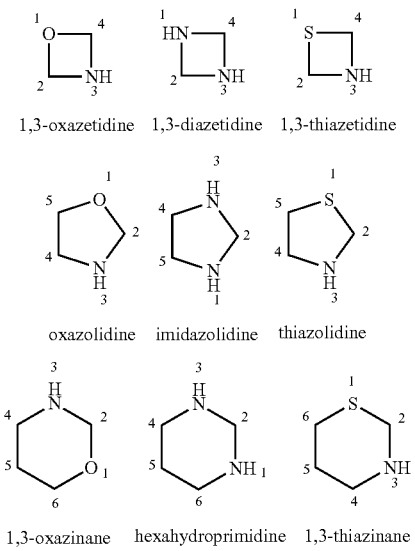

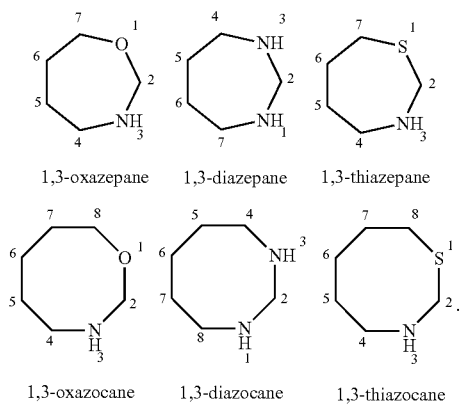

For the methods described herein, the sulfidogenesis inhibitor compound of formula 1 inhibits the production of hydrogen sulfide by a sulfur-utilizing prokaryote.

Further, the sulfur-utilizing prokaryote produces sulfide through reduction of sulfate, thiosulfate, sulfur, bisulfite, an organosulfur compound, or a combination thereof.

For the methods, the sulfidogenesis inhibitor compound of Formula 1 is administered by injecting an injection fluid into the water injection system, hydrocarbon extraction system, or the hydrocarbon production system.

The hydrocarbon extraction system or the hydrocarbon production system treated in the methods disclosed herein is a subterranean hydrocarbon-containing formation, a water injection system, a well, a pipeline, a fluid separation vessel, a floating production storage vessel, an offloading vessel, a refinery, or a storage system. Preferably, the hydrocarbon extraction system or the hydrocarbon production system is a subterranean hydrocarbon-containing formation.

The injection fluid used in the methods comprises seawater, produced water, fresh water, brackish water, drilling fluid, completion fluid, or a combination thereof.

For the sulfidogenesis inhibitor compound of Formula 1 used in the methods and compositions described herein A is oxazolidine, imidazolidine, or thiazolidine.

The sulfidogenesis inhibitor compound of Formula 1 preferably has n be 1.

Methods and compositions containing the sulfidogenesis inhibitor compound of Formula 1 preferably have $R_3$ be hydrogen, methyl, or benzyl.

The sulfidogenesis inhibitor compound of Formula 1 preferably has $R_2$ and $R_4$ are hydrogen and $R_1$ and $R_5$ independently are hydrogen, substituted or unsubstituted $C_1$ to $C_6$ alkyl, substituted or unsubstituted phenyl, or substituted or unsubstituted benzyl. More preferably, $R_2$ and $R_4$ are hydrogen and $R_1$ and $R_5$ are independently hydrogen, unsubstituted $C_1$ to $C_6$ alkyl, unsubstituted phenyl, or unsubstituted benzyl, and most preferably, $R_2$ and $R_4$ are hydrogen and $R_1$ and $R_5$ are independently hydrogen, methyl, ethyl, propyl, butyl, phenyl, or benzyl.

The methods and compositions containing sulfidogenesis inhibitor compounds of Formula 1 preferably contain the compounds of Formula 2, wherein the compound of Formula 1 has a structure corresponding to Formula 2

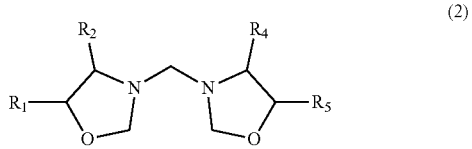

(2)

wherein $R_1$, $R_2$, $R_4$, and $R_5$ are independently hydrogen, substituted or unsubstituted alkyl, substituted or unsubstituted aryl, or substituted or unsubstituted alkaryl.

The methods and compositions used herein have sulfidogenesis inhibitor compounds of Formula 2 wherein $R_2$ and $R_4$ are hydrogen and $R_1$ and $R_5$ are independently hydrogen, substituted or unsubstituted $C_1$ to $C_6$ alkyl, or substituted or unsubstituted phenyl. Preferably, $R_2$ and $R_4$ are hydrogen and $R_1$ and $R_5$ are independently hydrogen, unsubstituted $C_1$ to $C_6$ alkyl, or unsubstituted phenyl; more preferably $R_2$ and $R_4$ are hydrogen and $R_1$ and $R_5$ are independently hydrogen, methyl, ethyl, propyl, butyl, phenyl, or benzyl.

A particularly preferred sulfidogenesis inhibitor compound of Formula 1 and 2 is 3,3'-methylenebis[5-methyloxazolidine] (MBO).

The hydrocarbon extraction system or the hydrocarbon production system treated in the methods disclosed herein is a subterranean hydrocarbon-containing formation and a sulfidogenesis inhibitor compound of Formula 2 wherein $R_2$ and $R_4$ are hydrogen and $R_1$ and $R_5$ are independently hydrogen, substituted or unsubstituted $C_1$ to $C_6$ alkyl, or substituted or unsubstituted phenyl are used.

Additionally, when the hydrocarbon extraction system or the hydrocarbon production system treated in the methods disclosed herein is a subterranean hydrocarbon-containing formation, a sulfidogenesis inhibitor compound of Formula 2 wherein $R_2$ and $R_4$ are hydrogen and $R_1$ and $R_5$ are independently hydrogen, unsubstituted $C_1$ to $C_6$ alkyl, or unsubstituted phenyl are used.

Further, when the hydrocarbon extraction system or the hydrocarbon production system treated in the methods disclosed herein is a subterranean hydrocarbon-containing formation, a sulfidogenesis inhibitor compound of Formula 2 wherein $R_2$ and $R_4$ are hydrogen and $R_1$ and $R_5$ are independently hydrogen, methyl, ethyl, propyl, butyl, phenyl, or benzyl are used.

For the methods described herein, the effective amount of the sulfidogenesis inhibitor compound of Formula 1 or Formula 2 is from about 1 to about 500 ppm, from about 1 to about 400 ppm, from about 1 to about 300 ppm, from about 1 to about 250 ppm, from about 1 to about 200 ppm, from about 1 to about 100 ppm, from about 10 to about 500 ppm, from about 10 to about 400 ppm, from about 10 to about 300 ppm, from about 10 to about 250 ppm, from about 10 to about 200 ppm, from about 10 to about 100 ppm, from about 25 to about 500 ppm, from about 25 to about 400 ppm, from about 25 to about 300 ppm, from about 25 to about 250 ppm, from about 25 to about 200 ppm, from about 25 to about 150 ppm, or from about 25 to about 100 ppm, based on the total amount of injection fluid injected into the formation or production system.

In particular, when the sulfidogenesis inhibitor compound of Formula 2 has $R_2$ and $R_4$ as hydrogen and $R_1$ and $R_5$ as independently hydrogen, substituted or unsubstituted $C_1$ to $C_6$ alkyl, or substituted or unsubstituted phenyl is used in the methods described herein, the effective amount of the compound of Formula 2 is from about 25 to about 250 ppm.

Additionally, when the sulfidogenesis inhibitor compound of Formula 2 has $R_2$ and $R_4$ as hydrogen and $R_1$ and $R_5$ as independently hydrogen, unsubstituted $C_1$ to $C_6$ alkyl, or unsubstituted phenyl is used in the methods described herein, the effective amount of the compound of Formula 2 is from about 25 to about 250 ppm.

Further, when the sulfidogenesis inhibitor compound of Formula 2 has $R_2$ and $R_4$ as hydrogen and $R_1$ and $R_5$ as independently hydrogen, methyl, ethyl, propyl, butyl, phenyl, or benzyl is used in the methods described herein, the effective amount of the compound of Formula 2 is from about 25 to about 250 ppm.

In particular, when the sulfidogenesis inhibitor compound of Formula 2 has $R_2$ and $R_4$ as hydrogen and $R_1$ and $R_5$ as independently hydrogen, substituted or unsubstituted $C_1$ to $C_6$ alkyl, or substituted or unsubstituted phenyl is used in the methods described herein, the effective amount of the compound of Formula 2 is from about 25 to about 150 ppm.

Additionally, when the sulfidogenesis inhibitor compound of Formula 2 has $R_2$ and $R_4$ as hydrogen and $R_1$ and $R_5$ as independently hydrogen, unsubstituted $C_1$ to $C_6$ alkyl, or unsubstituted phenyl is used in the methods described herein, the effective amount of the compound of Formula 2 is from about 25 to about 150 ppm.

Further, when the sulfidogenesis inhibitor compound of Formula 2 has $R_2$ and $R_4$ as hydrogen and $R_1$ and $R_5$ as independently hydrogen, methyl, ethyl, propyl, butyl, phenyl, or benzyl is used in the methods described herein, the effective amount of the compound of Formula 2 is from about 25 to about 150 ppm.

Typically, since the sulfidogenesis inhibitor compounds of Formula 1 and 2 are acting as sulfidogenesis inhibitors in the subterranean reservoir, the concentration of the compounds is significantly less than the concentration used when the compounds are used to scavenge hydrogen sulfide.

The sulfidogenesis inhibitor compound of Formula 1 or Formula 2 is injected into the water injection system, the hydrocarbon extraction system, or the hydrocarbon production system continuously with the injection fluid.

For the continuous injection of the sulfidogenesis inhibitor compound of Formula 1 or 2, the concentration of the compound of Formula 1 or 2 in the injection water can be from 1 to 100 ppm based on the total volume of the injection water. The amount of injection water used in the method is based on reservoir dynamics and hydrocarbon production displacement and can vary from 1 bbl of water to 10,000,000 bbl of water per day.

Alternatively, the sulfidogenesis inhibitor compound of Formula 1 or Formula 2 is injected into the water injection system, the hydrocarbon extraction system, or the hydrocarbon production system intermittently with the injection fluid. The injection of the compound of Formula 1 or Formula 2 is intermittently injected every 1 to 18 hours, every 1 to 12 hours, every 1 to 10 hours, every 1 to 8 hours, every 1 to 6 hours, every 1 to 4 hours, every 1 to 3 hours, every 1 to 6 days, every 1 to 5 days, every 1 to 4 days, every 1 to 3 days, every 1 to 2 days, every 1 to 6 weeks, every 1 to 5 weeks, every 1 to 4 weeks, or every 1 to 3 weeks.

In particular, when the sulfidogenesis inhibitor compound of Formula 2 has $R_2$ and $R_4$ as hydrogen and $R_1$ and $R_5$ as independently hydrogen, substituted or unsubstituted $C_1$ to $C_6$ alkyl, or substituted or unsubstituted phenyl is used in the methods described herein, the compound of Formula 2 is intermittently injected every 1 to 3 days.

Additionally, when the sulfidogenesis inhibitor compound of Formula 2 has $R_2$ and $R_4$ as hydrogen and $R_1$ and $R_5$ as independently hydrogen, unsubstituted $C_1$ to $C_6$ alkyl, or unsubstituted phenyl is used in the methods described herein, the compound of Formula 2 is intermittently injected every 1 to 3 days.

Further, when the sulfidogenesis inhibitor compound of Formula 2 has $R_2$ and $R_4$ as hydrogen and $R_1$ and $R_5$ as independently hydrogen, methyl, ethyl, propyl, butyl, phenyl, or benzyl is used in the methods described herein, the compound of Formula 2 is intermittently injected every 1 to 3 days.

The methods described herein further comprise administering an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof.

Compositions for inhibiting sulfidogenesis of a sulfur-utilizing prokaryote in a hydrocarbon-containing system comprising a water injection system, a hydrocarbon extraction system, or a hydrocarbon production system are also disclosed. The composition comprises an effective amount of a sulfidogenesis inhibitor compound of Formula 1; and an effective amount of a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof; the compound of Formula 1 having a structure corresponding to:

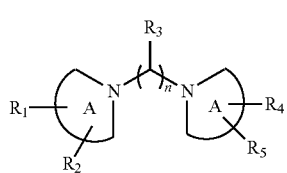

(1)

wherein A is a nitrogen-containing heterocycle of 1,3-oxazetidine, 1,3-diazetidine, 1,3-thiazetidine, oxazolidine, imidazolidine, thiazolidine, 1,3-oxazinane, hexahydropyrimidine, 1,3-thiazinane, 1,3-oxazepane, 1,3-diazepane, 1,3-thiazepane, 1,3-oxazocane, 1,3-diazocane, 1,3-thiazocane; $R_1$, $R_2$, $R_4$, and $R_5$ are independently hydrogen, substituted or unsubstituted alkyl, substituted or unsubstituted aryl, or substituted or unsubstituted alkaryl; $R_3$ is hydrogen, substituted or unsubstituted alkyl, substituted or unsubstituted aryl, or substituted or unsubstituted alkaryl; and n is an integer from 1 to 10.

The compositions for inhibiting sulfidogenesis of a sulfur-utilizing prokaryote in a hydrocarbon-containing system comprising a water injection system, a hydrocarbon extraction system, or a hydrocarbon production system comprise the sulfidogenesis inhibitor compound of Formula 1 and a biocide.

The methods and compositions described herein comprise a sulfidogenesis inhibitor compound, wherein the sulfidogenesis inhibitor compound consists of a compound of Formula 1 or Formula 2. The sulfidogenesis inhibitor compound can further consist of more than one compound of Formula 1 or Formula 2.

The sulfur-utilizing prokaryote can comprise a genus or species of bacteria and archaea capable of reducing sulfur compounds to produce sulfide.

Preferably, the sulfur-utilizing prokaryote can comprise a sulfate-reducing bacteria.

The hydrogen sulfide concentration in the hydrocarbon-containing system can be reduced by from about 1 to about 100 percent, from about 5 to about 100 percent, from about 10 to about 100 percent, from about 15 to about 100 percent, from about 20 to about 100 percent, from about 25 to about 100 percent, from about 30 to about 100 percent, from about 35 to about 100 percent, from about 40 to about 100 percent, from about 45 to about 100 percent, from about 50 to about 100 percent, from about 55 to about 100 percent, from about 60 to about 100 percent, from about 65 to about 100 percent, from about 70 to about 100 percent, from about 75 to about 100 percent, from about 80 to about 100 percent, from about 85 to about 100 percent, or from about 90 to about 100 percent, depending on the type and amount of sulfidogenesis inhibitor compound of Formula 1 or 2 added and the absence or presence of a sand surface for the microbes to attach to and grow.

In particular, when the sulfidogenesis inhibitor compound of Formula 2 has $R_2$ and $R_4$ as hydrogen and $R_1$ and $R_5$ as independently hydrogen, substituted or unsubstituted $C_1$ to $C_6$ alkyl, or substituted or unsubstituted phenyl is used in the methods described herein, the hydrogen sulfide concentration in the hydrocarbon-containing system can be reduced by from about 80 to about 100 percent.

Additionally, when the sulfidogenesis inhibitor compound of Formula 2 has $R_2$ and $R_4$ as hydrogen and $R_1$ and $R_5$ as independently hydrogen, unsubstituted $C_1$ to $C_6$ alkyl, or unsubstituted phenyl is used in the methods described herein, the hydrogen sulfide concentration in the hydrocarbon-containing system can be reduced by from about 80 to about 100 percent.

Further, when the sulfidogenesis inhibitor compound of Formula 2 has $R_2$ and $R_4$ as hydrogen and $R_1$ and $R_5$ as independently hydrogen, methyl, ethyl, propyl, butyl, phenyl, or benzyl is used in the methods described herein, the hydrogen sulfide concentration in the hydrocarbon-containing system can be reduced by from about 80 to about 100 percent.

The compounds of Formulae 1 and 2 are commercially available, for example, as ACTICIDE® OX from THOR Biocides. Further, the compounds can be prepared by multiple methods.

Methods of preparation of compounds of Formula 1 and 2 are described herein. For example, the bis-oxazolidine compounds can be prepared by a condensation reaction between a β-amino-alcohol (2 moles) and paraformaldehyde (3 moles) as depicted in Scheme 1. The water produced as result of condensation reaction is removed using a water-separator to drive the reaction to completion.

Scheme 1

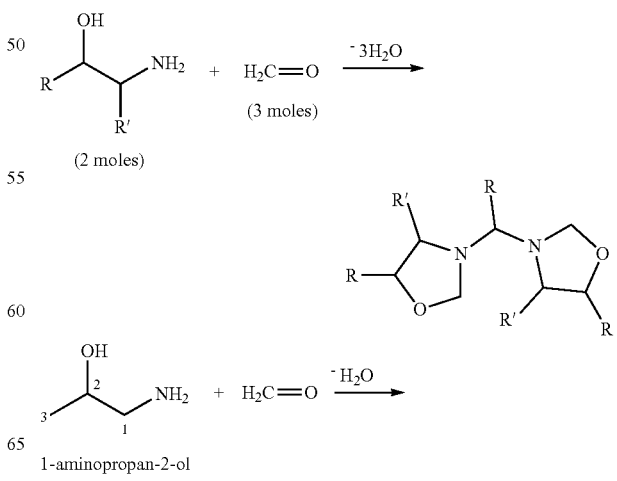

1-aminopropan-2-ol

-continued

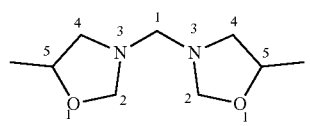

3,3'-Methylenebis[5-methyloxazolidine]

Synthesis of 3,3'-methylenebis[5-methyloxazolidine] (MBO). A mixture of amino-2-propanol (6 ml) and formaldehyde (3.0 g) is heated in toluene (100 ml) in flask with a Dean-Stark condenser for 30 minutes. Formaldehyde (1.5 g) is added to the reaction mixture. The mixture is refluxed in the flask until water is no longer lost from the Dean-Stark condenser. The reaction mixture is filtered and the solvent is removed on a rotary evaporator.

Other variants of 3,3'-methylenebis[5-methyloxazolidine] can be synthesized (as depicted in figure below) by replacing 1-aminopropan-2-ol with other amino-alcohols.

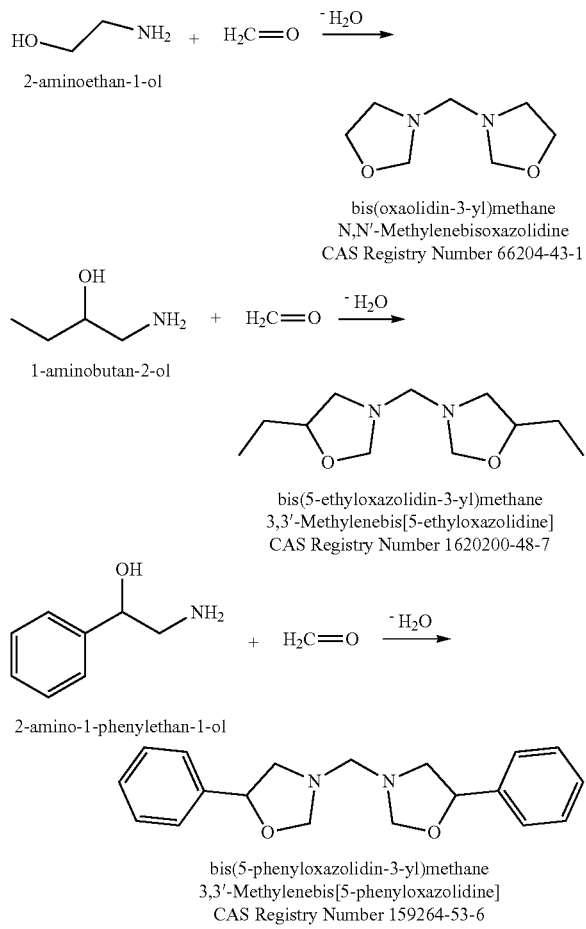

The compositions can be applied to a gas or liquid produced or used in a waste-water process, a farm, a slaughter house, a land-fill, a sewage collection system, a municipality waste-water plant, a coking coal process, a paper mill, or a biofuel process.

In another aspect, disclosed is a method of controlling biofouling, the method comprising providing an effective amount of a compound of Formula 1 or a composition described herein into a system. The method can include controlling microorganism proliferation in a system used in the production, transportation, storage, and separation of crude oil and natural gas. The method can include controlling microbe proliferation in a system used in a coal-fired process, a waste-water process, a farm, a slaughter house, a land-fill, a sewage collection system, a municipality waste-water plant, a coking coal process, a paper mill process, or a biofuel process.

The composition for inhibiting sulfidogenesis of a sulfur-utilizing prokaryote can comprise an effective amount of the sulfidogenesis inhibitor compound of Formula 1 and a component selected from the group consisting of an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, and a combination thereof.

The composition can comprise from about 20 to about 90 wt. % of the sulfidogenesis inhibitor compound and from about 10 to about 80 wt. % of the component, preferably from about 50 to about 90 wt. % of one or more sulfidogenesis inhibitor compound and from about 10 to about 50 wt. % of the component, and more preferably from about 65 to about 85 wt. % of one or more sulfidogenesis inhibitor compound and from about 15 to about 35 wt. % of the component.

The component of the composition can comprise an organic solvent. The composition can comprise from about 1 to 80 wt. %, from about 5 to 50 wt. %, or from about 10 to 35 wt. % of the one or more organic solvents, based on total weight of the composition. The organic solvent can comprise an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

The component of the composition can comprise a corrosion inhibitor. The composition can comprise from about 0.1 to 20 wt. %, 0.1 to 10 wt. %, or 0.1 to 5 wt. % of the corrosion inhibitors, based on total weight of the composition. A composition of the present disclosure can comprise from 0.1 to 10 percent by weight of the corrosion inhibitors, based on total weight of the composition. The composition can comprise 1.0 wt %, 1.5 wt %, 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, 7.0 wt %, 7.5 wt %, 8.0 wt %, 8.5 wt %, 9.0 wt %, 9.5 wt %, 10.0 wt %, 10.5 wt %, 11.0 wt %, 11.5 wt %, 12.0 wt %, 12.5 wt %, 13.0 wt %, 13.5 wt %, 14.0 wt %, 14.5 wt %, or 15.0 wt % by weight of the corrosion inhibitors, based on total weight of the composition. Each system can have its own requirements, and the weight percent of one or more additional corrosion inhibitors in the composition can vary with the system in which it is used.

The corrosion inhibitor can comprise an imidazoline compound, a quaternary ammonium compound, a pyridinium compound, or a combination thereof.

The corrosion inhibitor component can comprise an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (I) or an imidazoline derivative. Representative imidazoline derivatives include an imidazolinium compound of Formula (II) or a bis-quaternized compound of Formula (III).

The corrosion inhibitor component can include an imidazoline of Formula (I):

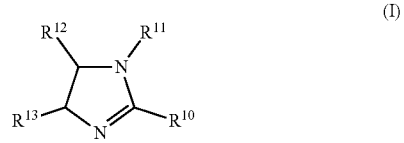

wherein $R^{10}$ is a $C_1$-$C_{20}$ alkyl or a $C_1$-$C_{20}$ alkoxyalkyl group; $R^{11}$ is hydrogen, $C_1$-$C_6$ alkyl, $C_1$-$C_6$ hydroxyalkyl, or $C_1$-$C_6$ arylalkyl; and $R^{12}$ and $R^{13}$ are independently hydrogen or a $C_1$-$C_6$ alkyl group. Preferably, the imidazoline includes an $R^{10}$, which is the alkyl mixture typical in tall oil fatty acid (TOFA), and $R^{11}$, $R^{12}$ and $R^{13}$ are each hydrogen.

The corrosion inhibitor component can include an imidazolinium compound of Formula (II):

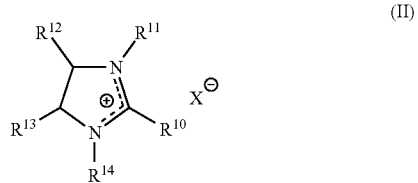

wherein $R^{10}$ is a $C_1$-$C_{20}$ alkyl or a $C_1$-$C_{20}$ alkoxyalkyl group; $R^{11}$ and $R^{14}$ are independently hydrogen, $C_1$-$C_6$ alkyl, $C_1$-$C_6$ hydroxyalkyl, or $C_1$-$C_6$ arylalkyl; $R^{12}$ and $R^{13}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The corrosion inhibitor can comprise a bis-quaternized compound having the formula (III):

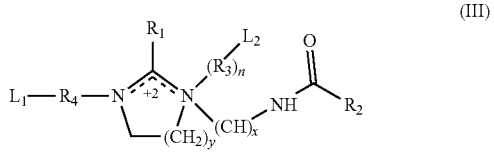

wherein $R_1$ and $R_2$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof; $R_3$ and $R_4$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof; $L_1$ and $L_2$ are each independently absent, H, —COOH, —SO$_3$H, —PO$_3$H$_2$, —COOR$_5$, —CONH$_2$, —CONHR$_5$, or —CON(R$_5$)$_2$; $R_5$ is each independently a branched or unbranched alkyl, aryl, alkylaryl, alkylheteroaryl, cycloalkyl, or heteroaryl group having from 1 to about 10 carbon atoms; n is 0 or 1, and when n is 0, $L_2$ is absent or H; x is from 1 to about 10; and y is from 1 to about 5. Preferably, $R_1$ and $R_2$ are each independently $C_6$-$C_{22}$ alkyl, $C_8$-$C_{20}$alkyl, $C_{12}$-$C_{18}$ alkyl, $C_{16}$-$C_{18}$alkyl, or a combination thereof; $R_3$ and $R_4$ are $C_1$-$C_{10}$ alkylene, $C_2$-$C_8$ alkylene, $C_2$-$C_6$ alkylene, or $C_2$-$C_3$ alkylene; n is 0 or 1; x is 2; y is 1; $R_3$ and $R_4$ are —C$_2$H$_2$—; $L_1$ is —COOH, —SO$_3$H, or —PO$_3$H$_2$; and $L_2$ is absent, H, —COOH, —SO$_3$H, or —PO$_3$H$_2$. For example, $R_1$ and $R_2$ can be derived from a mixture of tall oil fatty acids and are predominantly a mixture of $C_{17}H_{33}$ and $C_{17}H_{31}$ or can be $C_{16}$-$C_{18}$alkyl; $R_3$ and $R_4$ can be $C_2$-$C_3$ alkylene such as —C$_2$H$_2$—; n is 1 and $L_2$ is —COOH or n is 0 and $L_2$ is absent or H; x is 2; y is 1; $R_3$ and $R_4$ are —C$_2$H$_2$—; and $L_1$ is —COOH.

It should be appreciated that the number of carbon atoms specified for each group of formula (III) refers to the main chain of carbon atoms and does not include carbon atoms that may be contributed by substituents.

The corrosion inhibitor can comprise a bis-quaternized imidazoline compound having the formula (III) wherein $R_1$ and $R_2$ are each independently $C_6$-$C_{22}$ alkyl, $C_8$-$C_{20}$alkyl, $C_{12}$-$C_{18}$ alkyl, or Cm-Cis alkyl or a combination thereof; $R_4$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is —COOH, —SO$_3$H, or —PO$_3$H$_2$; and $L_2$ is absent or H. Preferably, a bis-quaternized compound has the formula (III) wherein $R_1$ and $R_2$ are each independently Cm-Cis alkyl; $R_4$ is —C$_2$H$_2$—; x is 2; y is 1; n is 0; $L_1$ is —COOH, —SO$_3$H, or —PO$_3$H$_2$ and $L_2$ is absent or H.

The corrosion inhibitor can be a quaternary ammonium compound of Formula (IV):

wherein $R_1$, $R_2$, and $R_3$ are independently $C_1$ to $C_{20}$ alkyl, $R_4$ is methyl or benzyl, and $X^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms, and X is Cl, Br or I. For the quaternary salts, R$^{5a}$, R$^{6a}$, R$^{7a}$, and R$_{8a}$ can each be independently selected from the group consisting of alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The corrosion inhibitor component can comprise a pyridinium salt such as those represented by Formula (V):

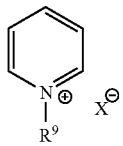

(V)

wherein $R^9$ is an alkyl group, an aryl group, or an arylalkyl group, wherein said alkyl groups have from 1 to about 18 carbon atoms and $X^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The corrosion inhibitor components can include additional corrosion inhibitors such as phosphate esters, monomeric or oligomeric fatty acids, or alkoxylated amines.

The corrosion inhibitor component can comprise a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a more broad distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The corrosion inhibitor component can include a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The corrosion inhibitor component can comprise an alkoxylated amine. The alkoxylated amine can be an ethoxylated alkyl amine. The alkoxylated amine can be ethoxylated tallow amine.

The component of the composition can comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol. The organic sulfur compound can constitute 0.5 to 15 wt. % of the composition, based on total weight of the composition, preferably about 1 to about 10 wt. % and more preferably about 1 to about 5 wt. %. The organic sulfur compound can constitute 1, 2, 3, 4, 5, 6, 7, 8, 9, 10, 11, 12, 13, 14 or 15 wt. % of the composition.

The composition can be substantially free of or free of any organic sulfur compound other than the compound of formula (1). A composition is substantially free of any organic sulfur compound if it contains an amount of organic sulfur compound below the amount that will produce hydrogen sulfide gas upon storage at a temperature of 25° C. and ambient pressure.

The component of the composition can further include a demulsifier. Preferably, the demulsifier comprises an oxyalkylate polymer, such as a polyalkylene glycol. The demulsifier can constitute from about 0.1 to 10 wt. %, from about 0.5 to 5 wt. %, or from about 0.5 to 4 wt. % of the composition, based on total weight of the composition. The demulsifier can constitute 0.5, 1, 1.5, 2, 2.5, 3, 3.5, 4, 4.5 or 5 wt. % of the composition.

The component of the composition can include an asphaltene inhibitor. The composition can comprise from about 0.1 to 10 wt. %, from about 0.1 to 5 wt. %, or from about 0.5 to 4 wt. % of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The component of the composition can include an additional paraffin inhibitor. The composition can comprise from about 0.1 to 10 wt. %, from about 0.1 to 5 wt. %, or from about 0.5 to 4 wt. % of an additional paraffin inhibitor, based on total weight of the composition. Suitable additional paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The component of the composition can include a scale inhibitor. The composition can comprise from about 0.1 to 20 wt. %, from about 0.5 to 10 wt. %, or from about 1 to 10 wt. % of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

The component of the composition can include an emulsifier. The composition can comprise from about 0.1 to 10 wt. %, from about 0.5 to 5 wt. %, or from about 0.5 to 4 wt. % of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

The component of the composition can include a water clarifier. The composition can comprise from about 0.1 to 10 wt. %, from about 0.5 to 5 wt. %, or from about 0.5 to 4 wt. % of a water clarifier, based on total weight of the composition. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

The component of the composition can include a dispersant. The composition can comprise from about 0.1 to 10 wt. %, from about 0.5 to 5 wt. %, or from about 0.5 to 4 wt. % of a dispersant, based on total weight of the composition. Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The component of the composition can include an emulsion breaker. The composition can comprise from about 0.1 to 10 wt. %, from about 0.5 to 5 wt. %, or from about 0.5 to 4 wt. % of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, anionic, cationic and non-ionic surfactants, and resins, such as phenolic and epoxide resins.

The component of the composition can include a hydrogen sulfide scavenger. The composition can comprise from about 1 to 50 wt. %, from about 1 to 40 wt. %, or from about 1 to 30 wt. % of a hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The component of the composition can include a gas hydrate inhibitor. The composition can comprise from about 0.1 to 25 wt. %, from about 0.1 to 20 wt. %, or from about 0.3 to 20 wt. % of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The component of the composition can include a kinetic hydrate inhibitor. The composition can comprise from about 5 to 30 wt. %, from about 5 to 25 wt. %, or from about 10 to 25 wt. % of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The component of the composition can include a biocide. The composition can comprise from about 0.1 to 35 wt. %, from about 10 to 35 wt. %, or from about 15 to 35 wt. % of a biocide, based on total weight of the composition. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, peroxides, biguanine, formaldehyde releasing preservatives, performic acid, peracetic acid, nitrate, and combinations thereof.

The component of the composition can include a pH modifier. The composition can comprise from about 0.1 to 20 wt. %, from about 0.5 to 10 wt. %, or from about 0.5 to 5 wt. % of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The component of the composition can include a surfactant. The composition can comprise from about 0.1 to 10 wt. %, from about 0.5 to 5 wt. %, or from about 0.5 to 4 wt. % of a surfactant, based on total weight of the composition. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block The component of the composition can also include an iron chelator. The iron chelator can be selected from gluconic acid, citric acid, ascorbic acid, tetrakis(hydroxymethyl)phosphonius sulfate (THPS), and combinations thereof.

Sulfidogenesis inhibitor compositions made according to the disclosure can further include additional functional agents or additives that provide a beneficial property. For example, additional agents or additives can be sequestrants, solubilizers, lubricants, buffers, cleaning agents, rinse aids, preservatives, binders, thickeners or other viscosity modifiers, processing aids, carriers, water-conditioning agents, foam inhibitors or foam generators, threshold agents or systems, aesthetic enhancing agents (i.e., dyes, odorants, perfumes), or other additives suitable for formulation with a corrosion inhibitor composition, and mixtures thereof. Additional agents or additives will vary according to the particular corrosion inhibitor composition being manufactured and its intend use as one skilled in the art will appreciate.

Alternatively, the compositions can not contain any of the additional agents or additives.

Additionally, the sulfidogenesis inhibitor compound can be formulated into a treatment fluid comprising the following components. These formulations include the ranges of the components listed and can optionally include additional agents.

| Component | 1 | 2 | 3 | 4 | 5 | 6 | 7 | 8 | 9 | 10 | 11 | 12 |
|---|---|---|---|---|---|---|---|---|---|---|---|---|
| Sulfidogenesis inhibitor compound | 30-90 | 30-90 | 30-90 | 30-90 | 30-90 | 30-90 | 65-85 | 65-85 | 65-85 | 65-85 | 65-85 | 30-90 |
| Organic solvent | 10-35 | | | | | | 10-35 | | | | | 10-35 |
| Corrosion inhibitor | 0.1-20 | 0.1-20 | | | | | 0.1-20 | 0.1-20 | | | | 0.1-20 |
| Asphaltene inhibitor | 0.1-5 | 0.1-5 | 0.1-5 | 0.1-5 | | | 0.1-5 | 0.1-5 | 0.1-5 | | | 0.1-5 |
| Paraffin inhibitor | | | | | | | | | | | | |
| Scale inhibitor | 1-10 | 1-10 | 1-10 | 1-10 | 1-10 | | 1-10 | 1-10 | 1-10 | 1-10 | | 1-10 |
| Emulsifier | | | | | | | | | | | | |
| Water clarifier | | | | | | | | | | | | |
| Dispersant | | | | | | | | | | | | |
| Emulsion breaker | | | | | | | | | | | | |
| Gas hydrate inhibitor | | | | | | | | | | | | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | |
| pH modifier | | | | | | | | | | | | |
| Surfactant | | | | | | | | | | | | |

| Component | 13 | 14 | 15 | 16 | 17 | 18 | 19 | 20 | 21 | 22 | 23 | 24 |
|---|---|---|---|---|---|---|---|---|---|---|---|---|
| Sulfidogenesis inhibitor compound | 30-90 | 30-90 | 30-90 | 30-90 | 30-90 | 30-90 | 65-85 | 65-85 | 65-85 | 65-85 | 65-85 | 65-85 |
| Organic solvent | | | | | | | | | | | | |
| Corrosion inhibitor | 0.1-20 | 0.1-20 | 0.1-20 | 0.1-20 | 0.1-20 | | 0.1-20 | 0.1-20 | 0.1-20 | 0.1-20 | 0.1-20 | 0.1-20 |
| Asphaltene inhibitor | 0.1-5 | | | | | | 0.1-5 | | | | | |
| Paraffin inhibitor | | | | | | | | | | | | |
| Scale inhibitor | 1-10 | 1-10 | | 1-10 | | | 1-10 | 1-10 | | | | 1-10 |
| Emulsifier | | | | | | | | | | | | |
| Water clarifier | | | | | | | | | | | | |
| Dispersant | | | | | | | | | | | | |
| Emulsion breaker | | | | | | | | | | | | |
| Gas hydrate inhibitor | 0.1-25 | 0.1-25 | 0.1-25 | | | | 0.1-25 | 0.1-25 | 0.1-25 | | 0.1-25 | |
| Biocide | | | | | | 0.5-35 | 0.5-5 | 0.5-5 | 0.5-5 | 0.5-5 | | |
| pH modifier | | | | | | | | | | | | |
| Surfactant | | | | | | | | | | | | | copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkylim inodipropionate.

Unless otherwise indicated, an alkyl group as described herein alone or as part of another group is an optionally substituted linear saturated monovalent hydrocarbon substituent containing from one to sixty carbon atoms and preferably one to thirty carbon atoms in the main chain or eight to thirty carbon atoms in the main chain, or an optionally substituted branched saturated monovalent hydrocarbon substituent containing three to sixty carbon atoms, and preferably eight to thirty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term alkoxy as used herein or alone or as part of another group is an —OR group, wherein the R group is a substituted or unsubstituted alkyl group as defined herein.

The terms "aryl" or "ar" as used herein alone or as part of another group (e.g., aralkyl) denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The term "aryl" also includes heteroaryl.

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino(—N($R_A$)($R_B$), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

The term "heterocyclo," "heterocycle," or "heterocyclyl," as used herein, refers to a monocyclic, bicyclic, or tricyclic group containing 1 to 4 heteroatoms selected from N, O, S(O)$_n$, P(O)$_n$, PR$^Z$, NH or NR$^Z$, wherein R$^Z$ is a suitable substituent. Heterocyclic groups include, but are not limited to, 1,3-oxazetidine, 1,3-diazetidine, 1,3-thiazetidine, oxazolidine, imidazolidine, thiazolidine, 1,3-oxazinane, hexahydropyrimidine, 1,3-thiazinane, 1,3-oxazepane, 1,3-diazepane, 1,3-thiazepane, 1,3-oxazocane, 1,3-diazocane, 1,3-thiazocane. Heterocyclic groups can be unsubstituted or substituted by one or more suitable substituents, preferably 1 to 3 suitable substituents, as defined above.

Having described the disclosure in detail, it will be apparent that modifications and variations are possible without departing from the scope of the invention defined in the appended claims.

EXAMPLES

The following non-limiting examples are provided to further illustrate the present disclosure.

Example 1: Sulfide Inhibition

Sample Preparation and Test Conditions. Field water samples were collected and shipped under anoxic conditions. Prior to setting up the bottle test, the water was sparged with carbon dioxide in a nitrogen environment overnight to remove the existing hydrogen sulfide. The water sample was then supplemented with 50 mg/L acetate, 5 mg/L propionate, and 5 mg/L butyrate and trace elements and vitamins. Fluids (100 mL) were aliquoted into 125 mL glass serum bottles containing a carbon steel 1018 ball bearing. Triplicate experiments were performed. Three bottles were left untreated and three bottles were treated each with 50 ppm and 80 ppm of the desired chemistry. Samples were incubated at 37° C. for 8 weeks.

Measurements and Results. A sulfide test kit (Code 4456-01, available from LaMotte) was used to test the efficacy of 3,3'-methylenebis[5-methyloxazolidine] (MBO) at a concentration of 50 ppm and 80 ppm based on the total weight of the sample, the results of which are shown in Table 1. The results demonstrate that an increased concentration of the MBO correspondingly decreases the sulfide concentration. Under the tested conditions, significant reduction (~94%) of biogenic sulfide concentration could be achieved with 80 ppm MBO treatment compared to the untreated sample.

TABLE 1

Average sulfide concentration (ppm) in untreated and MBO treated fluids after 8 weeks

| Treatment | Average Sulfide (ppm) | Average reduction in biogenic sulfide (%) |
|---|---|---|
| Untreated | 7.37 | — |
| MBO 50 ppm | 4.64 | 37.03 |
| MBO 80 ppm | 0.46 | 93.81 |

Example 2: Performance Testing in Field Water Samples from Another Source

Sample Preparation and Test Conditions. Field water samples were treated with additional organic acids (e.g., Source 2) and were collected and shipped under anoxic conditions. Prior to setting up the bottle test, the water was sparged with carbon dioxide in a nitrogen environment overnight to remove the existing hydrogen sulfide. The water sample was then supplemented with 1 mM acetate, trace elements, and vitamins. Fluids (100 mL) were aliquoted into 125 mL glass serum bottles containing a carbon steel 1018 ball bearing. Triplicate experiments were performed. Three bottles were left untreated and three bottles were treated each at a concentration of 80 ppm, 120 ppm, and 150 ppm of the desired chemistry based on the total weight of the sample. Samples were incubated at 37° C. for 6 weeks.

A sulfide test kit (Code 4456-01, available from LaMotte) was used to test the efficacy of 3,3'-methylenebis[5-methyloxazolidine] (MBO) of 80 ppm, 120 ppm and 150 ppm, the results of which are shown in Table 2. Under the tested conditions, significant reduction (~98%) of sulfide level could be achieved with 80 ppm MBO treatment.

TABLE 2

Average sulfide concentration (ppm) in untreated and MBO treated fluids after 6 weeks

| Treatment | Average Sulfide (ppm) | Average reduction in biogenic sulfide (%) |
|---|---|---|
| Untreated | 5.80 | — |
| MBO 80 ppm | 0.09 | 98.4 |
| MBO 120 ppm | 0.09 | 98.4 |
| MBO 150 ppm | 0.13 | 97.8 |

Example 3: Pressurized Bioreactor Testing

Sample preparation and test conditions. The sulfidogenesis inhibitor MBO was tested using a pressurized bioreactor system. Two sand packed bioreactors were used to establish a sour population of sulfate reducing microorganisms with a seawater mixture for one month. The pressurized bioreactors maintained a flow rate of 0.05 mL/minute and were held at a temperature of 30° C. and a pressure of 1000 psig. Once both bioreactors contained sufficient sulfide in the effluent, one bioreactor remained untreated (control bioreactor) and the other bioreactor was dosed with MBO (test bioreactor) throughout the remaining four months of the study. The sulfide levels were measured in the control and test bioreactors weekly. MBO was dosed continuously in increasing increments at 25, 50, 100, and 150 ppm for roughly five weeks of the experiment. Next, a 4-hour batch treatment of MBO at 500 ppm was also tested twice followed by a low continuous dosage of MBO at 80 ppm and 100 ppm, respectively. The pH of the system was then decreased from 8.5 to 7.5 and then 7.5 to 6.5 to observe the effect of pH on MBO's efficacy at inhibiting sulfidogenesis. Once the pH of the bioreactor had stabilized at 6.5, MBO was dosed continuously in decreasing increments at 150 ppm, 100 ppm, 80 ppm and 50 ppm. At the end of the study, the dosing of MBO was ceased to monitor when sulfide levels would return in the test bioreactor.

Measurements and Results. Table 3 shows the measured sulfide in the control and test bioreactors throughout the study. The pH measured in the system and the dosage of MBO throughout the study is recorded as well. The results show that dosage of MBO at 100 ppm did initially decrease sulfide levels in the test bioreactor to as low as 0.5 mg/L, but sulfide levels started to increase again afterwards. Two high batch dosages of MBO at 500 ppm followed by low continuous dosage at 80 and 100 ppm did not further decrease sulfide levels. As the pH of the system was lowered, the sulfide levels also began to lower. When the pH was 6.5, dosing MBO at 150 ppm dropped the sulfide levels to 0.5 mg/L where they stayed throughout the remainder of the study even through decreasing dosages of MBO.

TABLE 3

Sulfide concentration (mg/L) in the control and MBO treated bioreactors

| Day | Control Bioreactor Sulfide (mg/L) | Test Bioreactor Sulfide (mg/L) | Dosage of MBO (ppm) | pH of system |
|---|---|---|---|---|
| 1 | 20.8 | 13.3 | 0 | 8.5 |
| 2 | 31.2 | 25.3 | 0 | 8.5 |
| 4 | 38.8 | 40.9 | 0 | 8.5 |
| 7 | 45.5 | 44.4 | 0 | 8.5 |
| 9 | 41.0 | 44.2 | 0 | 8.5 |
| 11 | 43.8 | 37.8 | 0 | 8.5 |
| 14 | 47.7 | 44.1 | 0 | 8.5 |
| 16 | 46.7 | 44.5 | 0 | 8.5 |
| 18 | 47.1 | 45.0 | 0 | 8.5 |
| 22 | 36.9 | 37.3 | 0 | 8.5 |
| 23 | 39.0 | 35.8 | 0 | 8.5 |
| 25 | 36.2 | 35.5 | 0 | 8.5 |
| 28 | 36.9 | 36.0 | 0 | 8.5 |
| 30 | 36.3 | 34.9 | 25 | 8.5 |
| 21 | 36.0 | 44.6 | 25 | 8.5 |
| 35 | 37.8 | 45.7 | 25 | 8.5 |
| 37 | 38.5 | 46.2 | 50 | 8.5 |
| 38 | 37.2 | 48.7 | 50 | 8.5 |
| 42 | 36.7 | 44.8 | 50 | 8.5 |
| 44 | 34.4 | 44.2 | 100 | 8.5 |
| 45 | 36.3 | 41.0 | 100 | 8.5 |
| 46 | 41.8 | 10.3 | 100 | 8.5 |
| 49 | 36.9 | 3.1 | 100 | 8.5 |
| 51 | 36.4 | 0.7 | 100 | 8.5 |
| 52 | 35.5 | 0.5 | 100 | 8.5 |
| 53 | 38.1 | 3.1 | 100 | 8.5 |
| 56 | 35.8 | 5.3 | 100 | 8.5 |
| 58 | 35.7 | 4.9 | 150 | 8.5 |
| 60 | 36.3 | 1.0 | 150 | 8.5 |
| 63 | 34.4 | 21.5 | 150 | 8.5 |
| 65 | 36.4 | 19.9 | 150 | 8.5 |
| 67 | 39.9 | 25.7 | 150 | 8.5 |
| 70 | 34.9 | 29.1 | 150 | 8.5 |
| 72 | 34.2 | 29.4 | 0 | 8.5 |
| 74 | 34.8 | 21.9 | 0 | 8.5 |
| 77 | 38.0 | 32.0 | 0 | 8.5 |
| 78 | 38.4 | 37.2 | 500 (4 hours batch) + 80 | 8.5 |
| 79 | 40.2 | 37.8 | 80 | 8.5 |
| 80 | 41.1 | 23.0 | 80 | 8.5 |
| 81 | 46.6 | 27.7 | 80 | 8.5 |
| 84 | 41.9 | 31.8 | 80 | 8.5 |
| 86 | 43.0 | 32.0 | 80 | 3.5 |
| 88 | 41.7 | 29.1 | 0 | 8.5 |
| 91 | 40.1 | 25.6 | 0 | 8.5 |
| 93 | 38.2 | 30.7 | 500 (4 hours batch) + 100 | 8.5 |
| 94 | 43.0 | 24.1 | 100 | 8.5 |
| 95 | 48.8 | 24.2 | 100 | 8.5 |
| 98 | 42.9 | 20.3 | 100 | 8.5 |
| 100 | 44.3 | 20.1 | 100 | 7.5 |
| 101 | 43.4 | 9.9 | 100 | 7.5 |
| 102 | 43.0 | 16.6 | 100 | 7.5 |
| 105 | 51.3 | 22.5 | 100 | 7.5 |
| 107 | 44.1 | 20.2 | 100 | 6.5 |
| 108 | 44.5 | 23.4 | 100 | 6.5 |
| 109 | 46.6 | 20.9 | 100 | 6.5 |
| 112 | 46.2 | 18.2 | 100 | 6.5 |
| 114 | 40.2 | 16.3 | 150 | 6.5 |
| 115 | 41.0 | 7.7 | 150 | 6.5 |
| 116 | 42.3 | 2.9 | 150 | 6.5 |
| 119 | 43.3 | 0.7 | 150 | 6.5 |
| 121 | 44.6 | 0.5 | 150 | 6.5 |
| 122 | 41.7 | 0.5 | 150 | 6.5 |
| 123 | 44.3 | 0.5 | 150 | 6.5 |
| 126 | 39.4 | 0.5 | 150 | 6.5 |
| 128 | 32.6 | 0.5 | 100 | 6.5 |
| 129 | 32.0 | 0.5 | 100 | 6.5 |
| 130 | 32.9 | 0.5 | 100 | 6.5 |
| 133 | 31.7 | 0.5 | 100 | 6.5 |
| 135 | 34.5 | 0.5 | 80 | 6.5 |
| 136 | 30.5 | 0.5 | 80 | 6.5 |
| 137 | 30.1 | 0.5 | 80 | 6.5 |
| 140 | 30.7 | 0.5 | 80 | 6.5 |
| 141 | 31.5 | 0.5 | 50 | 6.5 |
| 144 | 30.9 | 0.5 | 50 | 6.5 |
| 147 | 31.6 | 0.5 | 50 | 6.5 |
| 150 | 31.3 | 0.5 | 0 | 6.5 |
| 151 | 31.6 | 0.5 | 0 | 6.5 |
| 154 | 31.6 | 0.5 | 0 | 6.5 |

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above methods without departing from the scope of the disclosure, it is intended that all matter contained in the above description shall be interpreted as illustrative and not in a limiting sense.

The invention claimed is:

1. A method of sulfidogenesis inhibition in a hydrocarbon-containing system comprising a water injection system, a hydrocarbon extraction system, or a hydrocarbon production system, the method comprising administering an effective amount of a sulfidogenesis inhibitor compound of Formula 1 into the water injection system, the hydrocarbon extraction system, or the hydrocarbon production system, the compound of Formula 1 having a structure corresponding to:

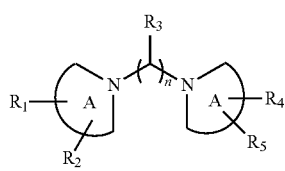

(1)

wherein
A is a nitrogen-containing heterocycle of 1,3-oxazetidine, 1,3-diazetidine, 1,3-thiazetidine, oxazolidine, imidazolidine, thiazolidine, 1,3-oxazinane, hexahydropyrimidine, 1,3-thiazinane, 1,3-oxazepane, 1,3-diazepane, 1,3-thiazepane, 1,3-oxazocane, 1,3-diazocane, 1,3-thiazocane;
$R_1$, $R_2$, $R_4$, and $R_5$ are independently hydrogen, substituted or unsubstituted alkyl, substituted or unsubstituted aryl, substituted or unsubstituted alkoxy, or substituted or unsubstituted alkaryl;
$R_3$ is hydrogen, substituted or unsubstituted alkyl, substituted or unsubstituted aryl, or substituted or unsubstituted alkaryl; and
n is an integer from 1 to 10.

2. The method of claim 1, wherein the sulfidogenesis inhibitor compound of formula 1 inhibits the production of hydrogen sulfide by a sulfur-utilizing prokaryote.

3. The method of claim 2, wherein the sulfur-utilizing prokaryote produces sulfide through reduction of sulfate, thiosulfate, sulfur, bisulfite, an organosulfur compound, or a combination thereof.

4. The method of claim 1, wherein the sulfidogenesis inhibitor compound of Formula 1 is administered by contacting the compound of Formula 1 with water in the water injection system or the sulfidogenesis inhibitor compound of Formula 1 is administered by injecting an injection fluid into the hydrocarbon extraction system or the hydrocarbon production system.

5. The method of claim 1, wherein the hydrocarbon extraction system or the hydrocarbon production system is a subterranean hydrocarbon-containing formation.

6. The method of claim 1, wherein the sulfidogenesis inhibitor compound of Formula 1 has a structure corresponding to Formula 2

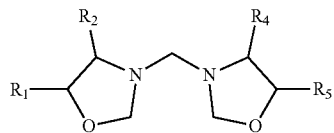

(2)

wherein
$R_1$, $R_2$, $R_4$, and $R_5$ are independently hydrogen, substituted or unsubstituted alkyl, substituted or unsubstituted aryl, substituted or unsubstituted alkoxy, or substituted or unsubstituted alkaryl.

7. The method of claim 6, wherein $R_2$ and $R_4$ are hydrogen and $R_1$ and $R_5$ are independently hydrogen, substituted or unsubstituted $C_1$ to $C_6$ alkyl, or substituted or unsubstituted phenyl.

8. The method of claim 6, wherein $R_2$ and $R_4$ are hydrogen and $R_1$ and $R_5$ are independently hydrogen, unsubstituted $C_1$ to $C_6$ alkyl, or unsubstituted phenyl.

9. The method of claim 6, wherein $R_2$ and $R_4$ are hydrogen and $R_1$ and $R_5$ are independently hydrogen, methyl, ethyl, propyl, butyl, phenyl, or benzyl.

10. The method of claim 9, wherein the effective amount of the sulfidogenesis inhibitor compound of Formula 2 is from about 1 to about 500 ppm based on the total amount of injection fluid injected into the formation or production system.

11. The method of claim 10, wherein the effective amount of the sulfidogenesis inhibitor compound of Formula 2 is from about 1 to about 250 ppm based on the total amount of injection fluid injected into the formation or production system.

12. The method of claim 10, wherein the effective amount of the sulfidogenesis inhibitor compound of Formula 2 is from about 1 to about 100 ppm based on the total amount of injection fluid injected into the formation or production system.

13. The method of claim 1, wherein the sulfidogenesis inhibitor compound of Formula 1 is injected into the water injection system, the hydrocarbon extraction system, or the hydrocarbon production system continuously with the injection fluid.

14. The method of claim 1, wherein the sulfidogenesis inhibitor compound of Formula 1 is injected into the water injection system, the hydrocarbon extraction system, or the hydrocarbon production system intermittently with the injection fluid.

15. The method of claim 14, wherein the injection of the sulfidogenesis inhibitor compound of Formula 1 is intermittently injected every one to three hours.

16. The method of claim 14, wherein the injection of the sulfidogenesis inhibitor compound of Formula 1 is intermittently injected every one to three days.

17. The method of claim 14, wherein the injection of the sulfidogenesis inhibitor compound of Formula 1 is intermittently injected every one to three weeks.

18. The method of claim 16, further comprising administering an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof.

* * * * *